US00PP36176P2

(12) United States Plant Patent
Read

(10) Patent No.: US PP36,176 P2
(45) Date of Patent: Oct. 1, 2024

(54) ***LEUCANTHEMUM* PLANT NAMED 'Real Solar'**

(50) Latin Name: ***Leucanthemum* X *superbum***
Varietal Denomination: Real Solar

(71) Applicant: Charles Richard Read, Bognor Regis (GB)

(72) Inventor: Charles Richard Read, Bognor Regis (GB)

( * ) Notice: Subject to any disclaimer, the term of this patent is extended or adjusted under 35 U.S.C. 154(b) by 0 days.

(21) Appl. No.: 18/543,409

(22) Filed: Dec. 18, 2023

(51) Int. Cl.
*A01H 5/02* (2018.01)
*A01H 6/14* (2018.01)

(52) U.S. Cl.
USPC ..... Plt./285
CPC ..... *A01H 6/14* (2018.05)

(58) Field of Classification Search
USPC ..... Plt./285
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new cultivar of *Leucanthemum* plant named 'Real Solar' that is distinguishable by its vigorous basal-branching and upright plant habit, uniformly long and narrow leaves with prominent dentate margins, a fully expanded inflorescence that is 8.5 cm-9 cm in diameter and is comprised of yellow to cream colored ray florets arranged around a dark mustard-yellow central disc. The ray florets of 'Real Solar' are arranged in three concentric whorls with overlapping ray floret petals and are yellow in color when first opening, becoming soft cream in color when fully expanded.

2 Drawing Sheets

Figure 1:
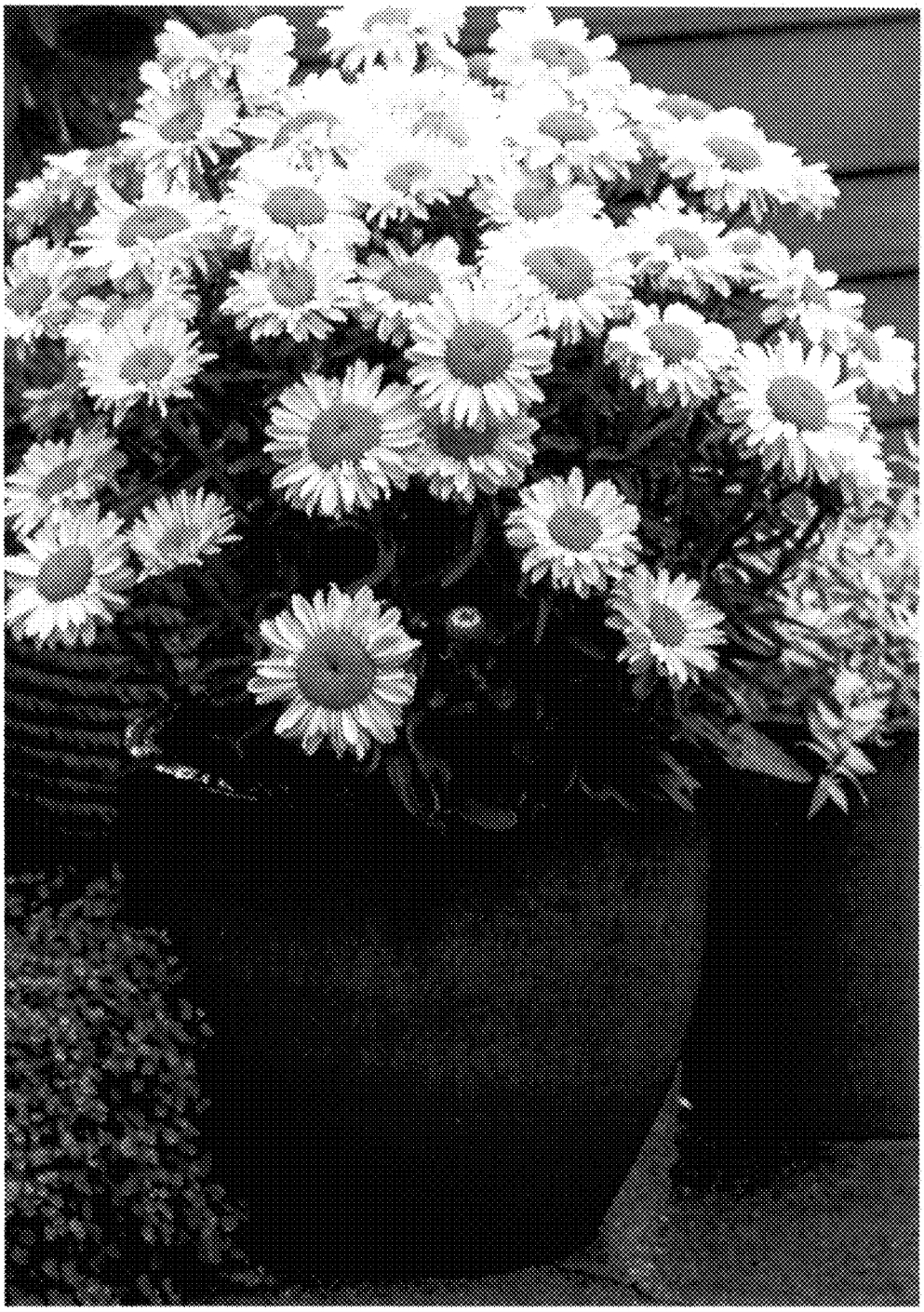

Genus and species: *Leucanthemum* x *superbum.*
Variety denomination: 'Real Solar'.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum* x *superbum* and will be referred to hereinafter by the cultivar name 'Real Solar'.

*Leucanthemum* is a genus within the family Asteraceae in which the commonly referred to "flower" is botanically the inflorescence which is comprised of outer showy white-colored ray florets surrounding a disc of smaller numerous mustard-yellow colored disc florets.

'Real Solar' arose and was selected from an ongoing breeding program which is conducted by the inventor at the inventor's nursery in West Sussex, United Kingdom. The breeding program commenced in 2006 with the aim of developing new and improved commercial varieties of *Leucanthemum* having new flower colors and shapes and more compact plant habits. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'Real Solar' is a seedling selection that resulted from the controlled pollination of a single plant of the inventor's proprietary *Leucanthemum* seedling code L1109-4 (unreleased and unpatented) as the female parent having white single flowers, using pollen from a single plant of the inventor's proprietary *Leucanthemum* seedling code L9023-3 (unreleased and unpatented) as the male parent having cream-colored single flowers. The inventor selected 'Real Solar' in 2017 for its combination of vigorous basal branching, uniformly narrow foliage, and late flowering strong stemmed inflorescences which are yellow in bud and which open as whorls of overlapping yellow ray florets.

'Real Solar' was first asexually propagated by the inventor in West Sussex, United Kingdom in 2020 using the method of vegetative division and subsequently by basal shoot cuttings. Since that time under careful observation 'Real Solar' has been determined uniform, stable and true to type in subsequent generations of asexual propagation.

SUMMARY

The following traits have been repeatedly observed and represent the distinguishing characteristics of 'Real Solar'. In combination, these traits set 'Real Solar' apart from all other existing varieties of *Leucanthemum* known to the inventor. 'Real Solar' has not been tested under all possible conditions and phenotypic differences may be observed with variations in environmental, climatic, and cultural conditions, however, without any variance in genotype.

1. 'Real Solar' exhibits vigorous basal-branching and upright plant habit.
2. A mature plant of 'Real Solar' is 76 cm in height and 38 cm in diameter.
3. The leaves of 'Real Solar' are uniformly long and narrow and have prominent dentate margins.
4. A fully expanded inflorescence of 'Real Solar' is 8.5 cm-9 cm in diameter and is comprised of yellow to cream colored ray florets arranged around a dark mustard-yellow central disc.
5. The ray florets of 'Real Solar' are arranged in three concentric whorls with overlapping ray floret petals.

6. The ray florets of 'Real Solar' are yellow in color when first opening, becoming cream in color when fully expanded.
7. The inflorescences of 'Real Solar' are carried on a strong stiff stems and are long-lasting, wind-resistant and suitable for cutting and use as cut flowers.
8. 'Real Solar' flowers from July to September.
9. 'Real Solar' is hardy in USDA Zone 5 (−20° F. or −28° C.).

BRIEF DESCRIPTION OF THE PHOTOGRAPHS

The accompanying color photographs were taken in July 2022 in Santa Barbara, California. The photographs illustrate the overall appearance of 'Real Solar' showing the color of foliage and inflorescence as true as is reasonably possible to obtain in color reproductions of this type. The illustrated plants had been grown in 2-gallon containers out of doors, without any pruning or use of chemical growth regulators. The colors in the photographs may differ from color values cited in the detailed botanical description, which accurately describe the actual color of 'Real Solar'.

FIG. 1 illustrates an eighteen-month-old plant of 'Real Solar' (from planting initial rooted cuttings). The illustrated plant has been transplanted from its 2-gallon growing container into an ornamental 3-gallon container. The illustrated plant is growing outdoors in full sun in Santa Barbara, California.

Figure 2:
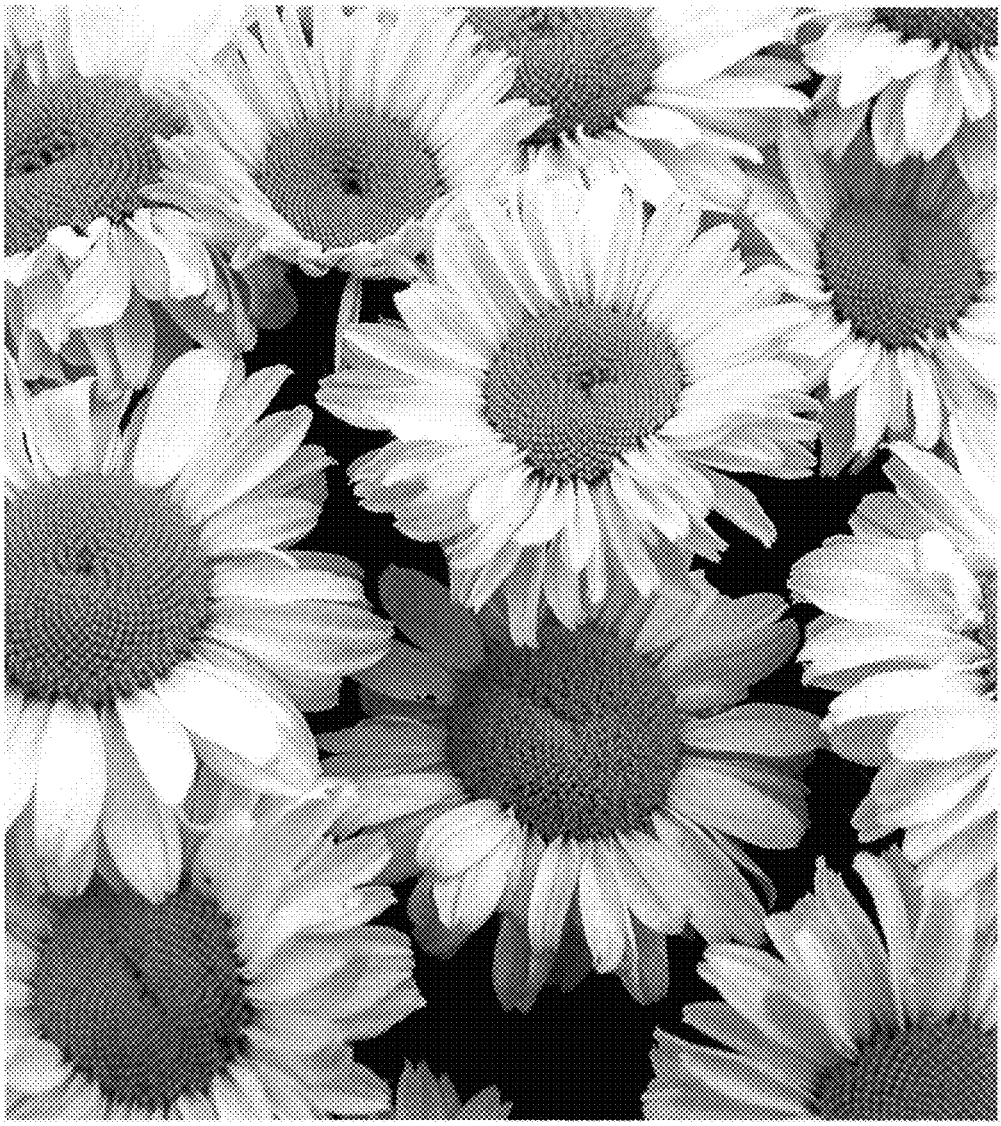

FIG. 2 depicts a close-up view of the inflorescences of 'Real Solar' and shows the colors of the ray florets when yellow as the inflorescence first opens, then fading to cream when the inflorescence is fully expanded. FIG. 2 also depicts the occasional folding of certain semi-quilled ray floret petals.

BOTANICAL DESCRIPTION OF THE PLANT

The following is a detailed botanical description of the new cultivar 'Real Solar'. Observations, measurements, values and comparisons were collected in Santa Barbara, California during September 2022, from an eighteen-month-old plant growing outdoors in a 2-gallon container. Color determinations are made in accordance with The 2007 Royal Horticultural Society Colour Chart from London, England, except where general color terms of ordinary dictionary significance are used.

Botanical classification:

*Family*.—Asteraceae (formerly Compositae).

*Genus*.—*Leucanthemum*.

*Species*.—x *superbum*.

*Denomination*.—'Real Solar'.

*Common name*.—Shasta daisy.

*Habit*—Vigorous basal-branching and upright growth habit.

*Commercial category*.—Perennial.

*Use*.—For garden and landscape.

*Suggested commercial container size*.—4-inch, 1 gallon, 2-gallon containers.

*Parentage*.—*Leucanthemum* x *superbum* 'Real Solar' is a seedling selection resulting from the controlled cross-pollination of the following parents: Male parent: inventor's proprietary *Leucanthemum* seedling code L9023-3. Female parent: inventor's proprietary *Leucanthemum* seedling code L1109-4.

*Propagation method*.—Basal shoot cuttings and division.

*Rooting system*.—Fine and fibrous.

*Vigor*.—Vigorous.

*Time to develop roots* (*range*).—14 to 20 days are needed for an initial cutting to develop roots.

*Temperature to develop roots* (*range*).—The recommended air temperature is 20° C. to 21° C.

*Crop time* (*range*).—10-12 weeks to produce a flowering plant in a 1-gallon container starting from a rooted cutting or 12-14 weeks to produce a full plant in a 2-gallon container.

*Plant dimensions* (*eighteen months*).—40 cm in height and 35 cm in width.

*Cultural requirements*.—Grow in full sun and rich, moist moderately fertile well-draining soil.

*Pest or disease resistance and susceptibility*.—No specific disease or pest resistance or susceptibility has been observed or is known to the inventor.

*Hardiness*.—USDA Zone 5.

Stems, branches:

*Description*.—Plant is pinched or stopped at first node close to soil level which encourages vigorous basal branching. Lateral branches borne on basal branches. All basal and lateral stems bear terminal inflorescences.

*Original stem below first pinch or stop*.—Shape: Short cylindrical. Dimensions: 1-2 cm in length, 1 cm in diameter. Surface: Lignified, rough, color 197B.

*Basal stems and lateral stems*.—Shape: Terete. Dimensions: 30-35 cm in length (base to calyx), 7 mm in diameter towards base, 4-5 mm in diameter immediately below calyx. Color: 137C. Surface: Pubescent, hairs 1.0-1.5 mm in length, fine, color NN155D. Strength: Rigid towards base, stiff, wiry towards apex.

Foliage:

*Type* (*division*).—Simple.

*Arrangement*.—Alternate.

*Internode length*.—1 cm. (average).

*Margin*.—Dentate, teeth approximately 1 cm apart, prominent, length (beyond leaf margin) up to 4 mm, width at base, 1.0-1.5 mm, aspect pointing towards leaf apex, teeth margin glabrous.

*Apex*.—Acute.

*Base*.—Cuneate.

*Leaf attachment*.—Sessile.

*Leaf color* (*both surfaces*).—136B.

*Leaf shape*.—Narrowly lanceolate, almost linear.

*Leaf dimensions*.—9.5 cm in length, 1.5 cm in width.

*Leaf venation*.—Pinnate branching from midrib, then longitudinally parallel.

*Vein color* (*both surfaces*).—136B.

*Leaf surface* (*adaxial surface*).—Glabrous, semi-glossy.

*Leaf surface* (*abaxial surface*).—Puberulent overall, pubescent midrib, hairs short, fine color NN155D.

Inflorescence:

*Inflorescence type*.—Capitulum, flattened dome, consisting of ray florets and disc florets.

*Inflorescence quantity* (*average at* 10 *weeks of age*).—45, including colored buds.

*Inflorescence diameter* (*fully opened*).—8.5 cm -9.0 cm including disc diameter 38 mm.

*Inflorescence height* (*including calyx*).—2.5 cm.

*Inflorescence aspect*.—Upright.

*Inflorescence colors*.—Ray florets on emergence: Yellow, 9B. Ray florets when fully developed: Cream, between NN155A and 2D. Central disc: Mustard-yellow, midway between 21A and 26A.

*Blooming season*.—Early-mid summer, reflowers in the fall.

*Lastingness of inflorescence, persistence*.—10-14 days on or off the plant, ray florets are persistent.

Bud:

*Bud dimensions*.—8 mm in height and 13 mm in diameter.

*Bud shape*.—Flattened sphere.

*Bud color* (*mass of involucral bracts, prior to ray florets emergence*).—137C. Involucral bract margin color 183A.

*Bud color* (*first ray florets showing*).—9B.

*Bud surface*.—Glabrous.

Peduncle:

*Peduncle shape*.—Terete.

*Peduncle length* (*from uppermost leaf to base of calyx*).—6.5 cm to 7.0 cm.

*Peduncle diameter*.—3.0 mm to 3.5 mm.

*Peduncle surface*.—Pubescent, hairs 1.0-1.5 mm in length, fine, color NN155D.

*Peduncle strength*.—Strong, stiff and wiry.

*Peduncle color*.—136B.

Peduncle bracts:

*Arrangement, quantity*.—One single bract attached 2-4 cm. below calyx; one or two bracts attached immediately below calyx.

*Attachment*.—Sessile.

*Shape*.—Lanceolate but contorted (twisted).

*Margin*.—Minutely dentate.

*Apex*.—Acute.

*Base*.—Truncate.

*Color* (*both surfaces*).—136B.

*Dimensions*.—Single bract 2-4 cm below calyx: 25 mm in length, 5 mm in width. Bracts at base of calyx: 5 mm in length, 2.5 mm in width.

*Surface* (*both surfaces*).—Glabrous.

Ray florets:

*Ray floret arrangement*.—Whorled, consisting of three concentric whorls of broad strap-like, occasionally longitudinally folded ray florets. Occasionally, an inflorescence may consist of two full whorls and the third uppermost whorl which carries a reduced number of ray florets.

*Quantity*.—About 85 to 90 of which 30-35 florets in each of the lower pairs of whorls, 20 florets in uppermost whorl.

*Shape*.—Ligules broadly lanceolate and occasionally gently longitudinally folded.

*Aspect*.—Emerge yellow and upward-facing becoming cream and horizontal when fully open.

*Corolla tube dimensions*.—4 mm-5 mm in length, 1 mm in diameter.

*Corolla tube color*.—143C (outer surface), 139A (inner surface and at base).

Ray floret petals:

*Shape*.—Strap-like, occasionally longitudinally furrowed, semi-quilled.

*Arrangement*.—Three whorls, petals overlapping in each whorl.

*Surface* (*both surfaces*).—Glabrous.

*Apex*.—Truncate or notched. Notch 1.5-2.0 mm in depth.

*Apex margin color*.—9B.

*Base*.—Attenuate.

*Margin*.—Entire.

*Dimensions*.—Up to 28 mm in length, 11 mm in width.

*Color* (*first open, both surfaces*).—9B.

*Color* (*petals fully expanded, both surfaces*).—Cream, between NN155A and 2D.

Involucral bracts:

*Quantity*.—Approximately 120 per inflorescence, overlapping, fused at base.

*Bract color* (*abaxial and adaxial surfaces*).—Ranges between 139C and 138B, except margins 151D.

*Bract length*.—5-8 mm.

*Bract width*.—3 mm.

*Bract apex*.—Rounded with tiny cilia, cilia color 183A.

*Bract base*.—Obtuse.

*Bract surface* (*both surfaces*).—Glabrous, translucent, waxy towards margins.

*Bract shape*.—Lanceolate.

*Bract margin*.—Entire, smooth, color 151D.

Disc florets:

*Disc diameter*.—38 mm.

*Disc floret quantity*.—Approximately 800 per inflorescence, massed at center of receptacle.

*Disc floret dimensions*.—6-7 mm in length, 1 mm in diameter.

*Disc floret shape*.—Tubular.

*Disc floret petal quantity*.—Ranges from 3 to 5 in number, basally fused.

*Disc floret petal dimensions*.—6 mm in length, 0.75 mm-1.0 mm in width.

*Disc floret petal color*.—Midway between 21A and 26A.

*Disc floret petal apex*.—Acute.

*Disc floret petal base*.—Truncate.

*Disc floret corolla tube*.—4 mm in length, 0.75 mm in diameter, color 145B to 145C.

Reproductive organs:

*Ray florets*.—Androecium (stamens, anthers, filaments, pollen): Absent. Pistil: 1, 3 mm in length, hair-like, diameter less than 0.2 mm., color light brown. Stigma: 2 mm in length, forked, branches recurved, diameter less than 0.2 mm, color 145B. Ovary: Not observed.

*Disc florets*.—General: Stigma, style, and ovary not observed. Stamens: 5, filaments length 3 mm and very fine diameter, color 154C. Anthers, pollen: None observed.

Seed:

*Quantity*.—Sparse.

*Shape*.—Ovoid, length 1.5 mm.

*Color*.—203D.

COMPARISON WITH PARENTAL LINES

'Real Solar' may be compared with its parents by the color of its ray florets. Whereas the ray florets of 'Real Solar' are yellow in color, the ray florets of the male parent L9023-3 are white in color and the ray florets of the female parent, L1109-4 are cream in color. In addition, the flower stems of 'Real Solar' are stronger and stiffer than the flower stems of either of the parent varieties.

COMPARISON WITH OTHER KNOWN VARIETIES

The commercial varieties of *Leucanthemum* which the inventor considers to closely resemble 'Real Solar' are Leucanthemum Plant Named 'Leumayel' (U.S. Plant Pat. No. 19,242) and the Inventor's (as co-inventor) variety Leucanthemum Plant Named 'Real Dream' (U.S. Plant Pat. No. 25,664). All three varieties, 'Real Solar', 'Leumayel' and 'Real Dream' bear yellow to cream-colored single-type inflorescences. However, the inflorescence of 'Real Solar' is comprised of three whorls of yellow to cream colored ray florets, whereas the inflorescence of 'Leumayel' comprises one whorl of cream colored ray florets . In consequence, the inflorescences of 'Real Solar' present distinctly overlapping ray floret petals whereas the inflorescence of 'Leumayel' presents gaps between the ray floret petals. In addition, the inflorescence of 'Real Solar' is large (8.5 cm-in diameter) in comparison with the inflorescence of 'Real Dream' (8 cm in diameter).

I claim:

1. A new and distinct cultivar of *Leucanthemum* plant named 'Real Solar' as described and illustrated herein.

* * * * *